United States Patent
Veluswamy et al.

(10) Patent No.: US 10,570,358 B2
(45) Date of Patent: Feb. 25, 2020

(54) APPARATUS WITH A FLOW DIVERTER AND FLOW ELEMENTS FOR MIXING MULTIPHASE FLOWING PARTICLES, AND A METHOD THEREOF

(71) Applicant: RELIANCE INDUSTRIES LIMITED, Mumbai (IN)

(72) Inventors: Ganesh K. Veluswamy, Mumbai (IN); Ramchandra Khopkar Avinash, Mumbai (IN)

(73) Assignee: Reliance Industries Limited, Mumbai (IN)

( * ) Notice: Subject to any disclaimer, the term of this patent is extended or adjusted under 35 U.S.C. 154(b) by 389 days.

(21) Appl. No.: 15/117,152

(22) PCT Filed: Mar. 3, 2015

(86) PCT No.: PCT/IB2015/051535
§ 371 (c)(1),
(2) Date: Aug. 5, 2016

(87) PCT Pub. No.: WO2015/132718
PCT Pub. Date: Sep. 11, 2015

(65) Prior Publication Data
US 2017/0175061 A1      Jun. 22, 2017

(30) Foreign Application Priority Data

Mar. 4, 2014 (IN) .......................... 741/MUM/2014

(51) Int. Cl.
*B01F 5/06* (2006.01)
*B01F 5/04* (2006.01)
(Continued)

(52) U.S. Cl.
CPC ............. *C12M 21/02* (2013.01); *A01G 33/00* (2013.01); *B01F 5/0065* (2013.01);
(Continued)

(58) Field of Classification Search
CPC ...... C12M 21/02; C12M 27/00; C12M 29/14; C12M 23/18; C12N 1/12; A01G 33/00;
(Continued)

(56) References Cited

U.S. PATENT DOCUMENTS 1,454,196 A * 5/1923 Trood ................... B01F 5/0415
                                                48/189.4
1,932,655 A * 10/1933 Erickson ............... B01F 5/0473
                                                196/46

(Continued)

FOREIGN PATENT DOCUMENTS

FR       2906305    *  3/2008   ........... F01N 3/2066
FR       2910532 A1 *  6/2008   ............ B01F 5/0268
(Continued)

OTHER PUBLICATIONS

International Search Report and Written Opinion for PCT Application No. PCT/IB2015/051535, dated Jul. 7, 2015, 6 pages.

*Primary Examiner* — Charles Cooley
(74) *Attorney, Agent, or Firm* — Sheppard Mullin Richter & Hampton LLP

(57) ABSTRACT

An apparatus (100) for mixing multiphase flowing particles. The apparatus (100) comprises a conduit (100a) adapted to channelize the multiphase flowing particles. At least one flow diverter (101) is positioned in the conduit (100a), which is adapted to divert the flow of multiphase flowing particles into a plurality of flow streams. Further, at least one flow element (102) is disposed in the conduit (100a) along at least one of the plurality of flow streams, which is configured to inject fluid onto the plurality of flow streams at a velocity greater than the velocity of the plurality of flow streams. This induces a swirling flow of at least one of the plurality of flow streams, thereby facilitating mixing of the multiphase flowing particles in the conduit (100a).

10 Claims, 9 Drawing Sheets

(51) Int. Cl.
*B01F 5/00* (2006.01)
*B01F 3/00* (2006.01)
*C12M 1/00* (2006.01)
*C12M 1/02* (2006.01)
*C12N 1/12* (2006.01)
*A01G 33/00* (2006.01)

(52) U.S. Cl.
CPC .......... *B01F 5/0473* (2013.01); *B01F 5/0619* (2013.01); *C12M 27/00* (2013.01); *C12M 29/14* (2013.01); *C12N 1/12* (2013.01); *B01F 3/00* (2013.01); *B01F 2005/0636* (2013.01); *C12M 23/18* (2013.01)

(58) Field of Classification Search
CPC .. B01F 5/0619; B01F 3/00; B01F 2005/0636; B01F 5/0473; B01F 5/0057; B01F 5/0062; B01F 5/0065; B01F 5/0068
USPC ............................................ 366/165.1–165.2
See application file for complete search history.

(56) References Cited

U.S. PATENT DOCUMENTS

| | | | | |
|---|---|---|---|---|
| 3,230,972 A | * | 1/1966 | Davis, Jr. | B01F 5/0473 137/599.01 |
| 3,671,208 A | * | 6/1972 | Medsker | B01F 5/0473 123/590 |
| 4,019,720 A | * | 4/1977 | Levesque | B01F 5/0068 261/124 |
| 4,981,368 A | * | 1/1991 | Smith | B01F 5/0473 366/337 |
| 5,113,028 A | * | 5/1992 | Chen | B01F 5/0057 570/216 |
| 5,492,404 A | * | 2/1996 | Smith | B01F 5/0057 366/165.1 |
| 5,839,828 A | * | 11/1998 | Glanville | B01F 5/0473 366/340 |
| 8,642,326 B1 | | 2/2014 | Schaefer et al. | |
| 8,746,216 B2 | * | 6/2014 | Elsasser | B01F 3/02 123/568.11 |
| 9,745,879 B2 | * | 8/2017 | Shiva | F01N 3/2066 |
| 9,931,602 B1 | * | 4/2018 | Mazzei | B01F 5/0426 |
| 9,975,094 B2 | * | 5/2018 | Gillis | B01F 5/0473 |
| 2002/0121350 A1 | * | 9/2002 | Lamminen | B01F 5/0473 162/100 |
| 2002/0162795 A1 | | 11/2002 | Pollock | |
| 2011/0120944 A1 | | 5/2011 | Ma'ayan et al. | |
| 2011/0171082 A1 | * | 7/2011 | Shiraishi | B01F 5/0057 422/198 |
| 2011/0305102 A1 | * | 12/2011 | Berger | B01F 5/0405 366/154.1 |
| 2012/0288917 A1 | | 11/2012 | Krenbrink et al. | |
| 2016/0258454 A1 | * | 9/2016 | Veluswamy | F15D 1/0025 |
| 2017/0175061 A1 | * | 6/2017 | Veluswamy | B01F 5/0619 |
| 2018/0286522 A1 | * | 10/2018 | Laberge | G21B 3/008 |
| 2019/0075743 A1 | * | 3/2019 | Maddikeri | E02B 13/00 |

FOREIGN PATENT DOCUMENTS

| | | | | |
|---|---|---|---|---|
| WO | WO-2008034981 A1 | * | 3/2008 | ............ B01F 3/022 |
| WO | WO-2014092641 A1 | * | 6/2014 | ........... B01F 5/0473 |
| WO | WO-2015053683 A1 | * | 4/2015 | ........... F01N 3/2066 |

* cited by examiner

Line A

Line B

APPARATUS WITH A FLOW DIVERTER AND FLOW ELEMENTS FOR MIXING MULTIPHASE FLOWING PARTICLES, AND A METHOD THEREOF

TECHNICAL FIELD

The present disclosure generally relates to field of fluid mechanics. Particularly but not exclusively, the present disclosure relates to mixing of multiphase flowing particles. Further, embodiments of the disclosure disclose an apparatus for mixing multiphase flowing particles in a flow conduit.

BACKGROUND

Multiphase flow herein above and below is defined as flow of fluids and/or solid particles together as a mixture, but without being completely dissolved in each other. Multiphase flow often occurs as, but not limiting to two-phase flow and three-phase flow. In two-phase flow, either fluids alone or one fluid along with solid particles flow in a flow system, whereas in the three-phase flow, fluids i.e. a gas and a liquid together with solid particles flow in the flow system. Such multiphase flow generally happens in processes such as but not limiting to oil and gas production, where oil and gases that are produced are conveyed in long pipes and channels for subjecting them to further processes, in waste water treatment or sewage treatment plants, slurry and mineral ore transport industries, sludge transport in refining industry, and biological continuous flow cultivation systems.

It is often observed that in the multiphase flow, stratified flow of particles takes place. The stratified flow herein above and below is defined as a flow in which high density particles in the flow mixture may flow at the bottom of the flow channel, and low density particle in the flow mixture may flow above the high density particles. In such stratified flow, the high density particle in the flow mixture may form a secondary phase, whereas the low density particle may form a primary phase. Thus, in the multiphase flow, the secondary phase distribution can become segregated and lead to subsequent settling along the axis of flow. In addition, stratified flow results in poor mass transfer characteristics in the flow systems. Further, the settling down of flow particles in the bottom surface of the flow channel results in following requirements and associated problems such as frequent operations to de-settle the sludge formed in the flow channels, which increases cost of operation in one or more processes stated above. In addition, settling of high density particles in a biological continuous flow cultivation system, such as algae cultivation, results in poor efficiency of cultivation process. In these biological continuous flow cultivation systems, vertical mixing is important for better nutrient homogenization of photosynthetic organisms such as but not limiting to algae. But due to minimal or lack of vertical mixing in the raceway pond, the flow becomes completely stratified, which leads to poor mass transfer of high density particles i.e. algae (or other photosynthetic organisms) and nutrients during the flow.

To overcome the one or more problems stated above, settling of the high density flow particles at the bottom surface of the flow channel should be avoided. In conventional practice, one or more mechanical mixers such as but not limiting to a paddlewheel, is adapted to rotate in a predetermined direction. The movement of the paddlewheel may be along an axis including but not limiting to a horizontal axis, or in a semi-horizontal axis. Similarly a stirrer which is adapted to rotate in a predetermined direction, or along an axis including but not limiting to a vertical axis and a semi-vertical axis, may be employed. Further, a baffle, fixed or moving in a predetermined manner including but not limited to a periodic motion and a rotational motion, have been employed. Typically, all of such mechanical mixers are either partially or fully submerged in a flow channel, and are adapted to move or rotate in respective aforesaid manners for mixing purposes. However, these conventional mechanical mixers require high energy for mixing the flow particles in the flow channel, which increases the cost of the process. Further, the use of mechanical mixers creates mixing only in the local zones around the mixer. Hence, for large-scale processes it is imperative that a large number of such mechanical mixers should be installed. However, in the large scale process it is imperative that power consumption for mixing should be minimum, and yet optimal results should be achieved. However, the use of multiple mixers consumes more energy, and makes the process economically insignificant. In addition to the high energy consumption, utilization of mechanical mixers may lead to problems including but not limiting to, inefficient mixing based on vortices formed behind the mixing blades and settling of solid mass at areas not within the reach of the mixers that have limited dimensions (such as diameters etc.), cavitation and raising of liners in lined bodies of liquid etc.

Further, in fluid mediums such as but not limiting to containers, ponds, wells, reservoirs and vessels it is known to use a means to disturb the fluid to facilitate mixing of the particles present in such fluid mediums. For example, means to disturb the fluid can be such as but not limiting to valves and nozzle arrangement, which can generate disturbance in the fluid medium by further providing fluid inside the fluid mediums. Such an arrangement facilitates mixing of the particles in the fluid medium. However, these conventional means to disturb the fluid require high energy for mixing the particles in the fluid medium, since the fluid has to be impinged at higher velocities, and the particles in the fluid medium would induce resistance since they are settled. This increases the cost of the process and accurate placement of disturbance means to have homogeneous or improved mixing is also a challenge. Further, the resultant mixing may only be achieved at localized regions and may not be entirely satisfactory for continuous flow systems.

As an example, consider a flow cultivation system where biological organisms such as but not limiting to photosynthetic organisms are cultivated in a biological continuous flow cultivation systems such as but not limiting to raceway ponds. In the biological continuous flow cultivation systems, there is a requirement for always keeping the solid particles in the suspended state i.e. solid particles should not be settled at bottom of the raceway ponds. Thus, the flow particles in the raceway ponds are mixed by a mechanical mixer installed in the raceway ponds. In general, mechanical mixer is partially submerged or else fully submerged in pond water at a fixed location, and is adapted to rotate at a fixed speed for mixing purposes. The mixing created by the mechanical mixer is thus localized, i.e., effective only for a small distance in the vicinity of the mechanical mixer. In the rest of the pond, although the flow is turbulent, the vertical mixing is not sufficient for optimal growth of photosynthetic organism. For achieving a uniform and efficient mixing through-out in the raceway pond, a plurality of mechanical mixers are required to be installed at multiple locations to generate turbulence, which in turn proves to be cost-ineffective. However, for a large-scale cultivation for fuel applications, it is imperative that the energy consumption in mixing is kept at minimum and yet optimal growth of algae is achieved. In addition to the high energy consumption, utilization of multiple mechanical mixers may lead to problems including but not limited to inefficient mixing based on vortices formed behind a paddlewheel and settling of solid particles at areas not within the reach of the mechanical mixers that have a limited diameter, cavitation and raising of liners in lined bodies of liquid etc. As explained above the mechanical mixer consumes high energy which in turn increases cost of cultivation of photosynthetic organism.

Limitations of existing conventional mechanical mixers are explained with the help of cultivation of photosynthetic organism (one of the field of applications of the mechanical mixers) as an example. However, such example should not be construed as only application. Thus, person skilled in the art can envisage various other applications where such limitation exists.

In light of foregoing discussion, there exists a need to develop an improved apparatus for mixing multiphase flowing particles in a conduit to overcome one or more limitations as stated above.

SUMMARY

The one or more limitations of conventional mixing apparatuses are overcome and additional advantages are provided through the present disclosure. Additional features and advantages are realized through the techniques of the present disclosure. Other embodiments and aspects of the disclosure are described in detail herein and are considered a part of the claimed disclosure.

In one non-limiting embodiment of the present disclosure, there is provided an apparatus for mixing multiphase flowing particles, the apparatus comprises a conduit adapted to channelize the multiphase flowing particles, wherein the conduit comprises an inlet side and an outlet side. At least one flow diverter is positioned in the conduit, wherein the at least one flow diverter is adapted to divert the flow of multiphase flowing particles into a plurality of flow streams. Further, at least one flow element is disposed in the conduit along at least one of the plurality of flow streams, wherein the at least one flow element is configured to inject fluid onto the plurality of flow streams at a velocity greater than the velocity of the plurality of flow streams. This induces a swirling flow of at least one of the plurality of flow streams, thereby facilitating mixing of the multiphase flowing particles in the conduit.

In one embodiment of present disclosure, the at least one flow diverter is positioned at the bottom of the conduit.

In one embodiment of present disclosure, the at least one flow diverter is positioned proximal to inlet side of the conduit.

In one embodiment of present disclosure, the at least one flow element is positioned in at least one side of the conduit.

In one embodiment of present disclosure, a plurality of flow elements is provided on either side of the conduit. Each of the plurality of flow elements provisioned in one of the sides of the conduit is configured to be diagonally opposite to at least one of the plurality of the flow elements provisioned in other side of the conduit.

In one embodiment of present disclosure, the shape of the at least one flow diverter is at least one of triangular, rhombic and hexagonal.

In one embodiment of present disclosure, the at least one flow diverter is at least one of nozzles, orifices and jet impingers.

In one embodiment of present disclosure, the at least one flow element is positioned at a predetermined angle with respect to flow axis of plurality of flow streams, to induce swirling flow of at least one of the plurality of flow streams.

In another non-limiting embodiment of the present disclosure, there is provided a method for mixing multiphase flowing particles, the method comprising acts of channelizing the multiphase flowing particles by a conduit. Then, diverting the flow of the multiphase flowing particles into a plurality of flow streams by at least one flow diverter positioned in the conduit. Further, it comprises of injecting fluid onto the plurality of flow streams at a velocity greater than the velocity of the plurality of flow streams to induce a swirling flow of at least one of the plurality of flow streams, thereby facilitating mixing of the multiphase flowing particles in the conduit.

In one embodiment of present disclosure, the swirling flow of at least one of the plurality of flow streams is induced along the length of the conduit.

It is to be understood that the aspects and embodiments of the disclosure described above may be used in any combination with each other. Several of the aspects and embodiments may be combined together to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The novel features and characteristics of the disclosure are set forth in the appended description. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which.

Figure 1:
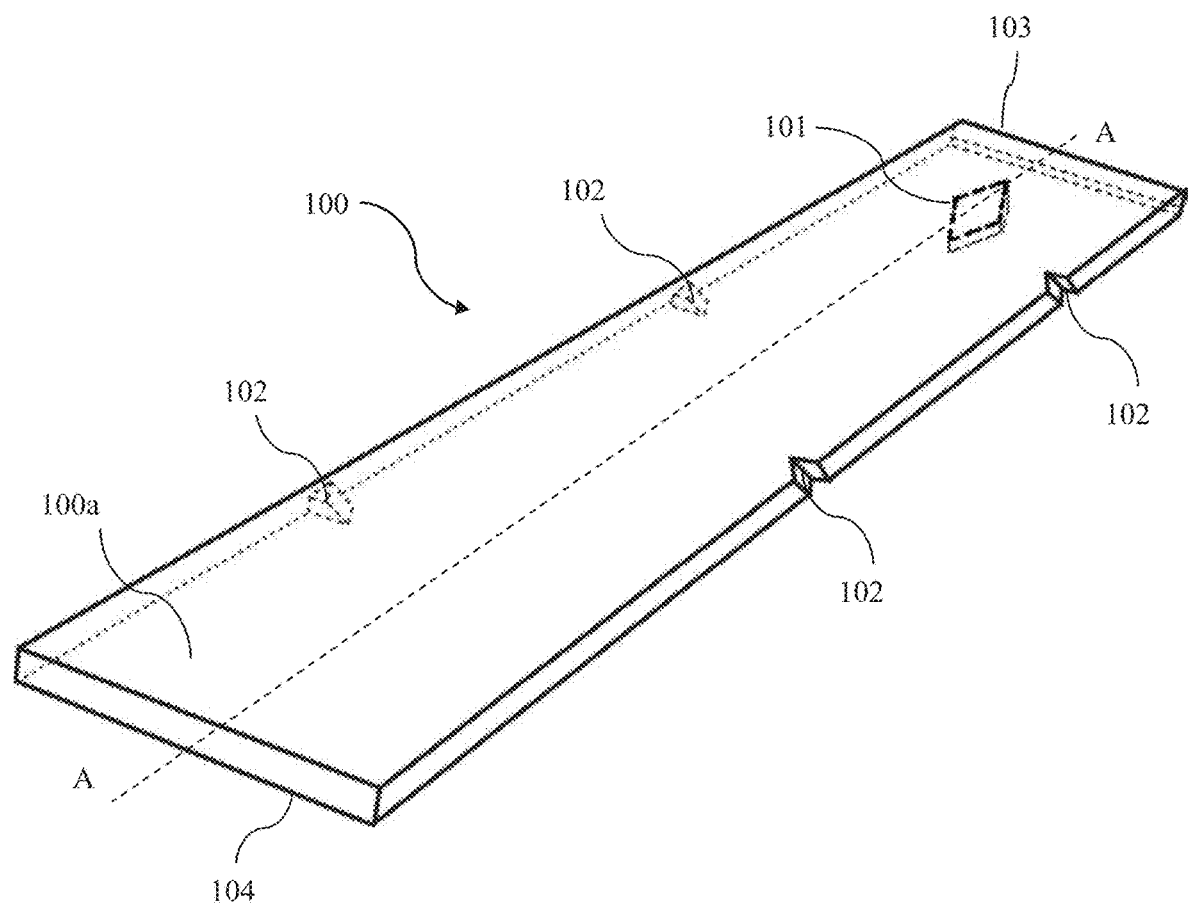
FIG. 1 illustrates perspective view of mixing apparatus for mixing multiphase flowing particles according to an embodiment of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

To overcome one or more limitations stated in the background, the present disclosure provides an apparatus for mixing multiphase flowing particles. In an embodiment of the present disclosure, the term multiphase flowing particles used herein above and below refers to a flow of a liquid-solid mixture, gas-liquid mixture, liquid-gas-solid mixture, flow of liquids of different densities and the like. Multiphase flow generally takes place when there is difference in densities of two or more phases flowing together as a mixture, without dissolving in one another. For example, in a mineral ore industry where metals in molten state are conveyed through long conduits for purification and other processes, and the impurities (slag) which are usually in solid phase flow along with the molten metal. In this case, molten metal forms the dispersion medium and impurities form the dispersed phase. Since densities of impurities (slag) are more than the density of molten metal, they accumulate at the bottom of conduit when the molten metal is conveyed. This results in only the molten metal being transported while impurities remain accumulated at the bottom surface in the conduit. The example of multiphase flow in mineral ore industry as described above should not be construed as the only application of the present disclosure and is envisaged only for the purpose of illustrating the multiphase flow.

The present disclosure relates to an apparatus for mixing these high density particles (hereinafter referred to as "secondary phase") with the main bulk flow (hereinafter referred to as "primary phase"). The flow of primary phase together with the secondary phase forms the multiphase flow. The mixing apparatus comprises of a conduit with an inlet and outlet for channelizing the multiphase flowing particles from one place to another place. The conduit has a predetermined cross-section and length. At least one flow diverter is placed at the bottom of conduit and proximal to inlet side of the conduit. The flow diverter is configured to divert the multiphase flowing particles into a number of flow streams along the longitudinal axis of the conduit. In addition, at least one flow element is provided in sides of the conduit along the flow stream. The flow element is configured to inject fluid onto the multiphase flowing particles at a velocity greater than the velocity of flow streams. In an embodiment of the present disclosure, injected fluid can be a fraction of multiphase flow (i.e. main flow), which is achieved by sucking a fraction of fluid containing secondary phase particles, from the main flow itself, and injecting it back into the main flow by the flow elements. In an alternate embodiment, the fluid injected on to the plurality of flow streams is taken from a separate fluid source. This injected fluid of high velocity generates swirling motion in the multiphase flowing particles, and causes agitation of secondary phase within the primary phase, resulting in the formation of a highly turbulent zone. This highly turbulent zone carries secondary phase from bottom to top and vice versa, and causes rotational motion of secondary phase in a vertical plane. This results in mixing the secondary phase with the primary phase. When the primary phase flows towards the outlet side of the conduit, the secondary phase is also carried by the primary phase towards the outlet. This prevents the stratification i.e. settling of relatively higher density particles at the bottom in a multiphase flow.

Use of terms such as "comprises", "comprising", or any other variations thereof in the description, are intended to cover a non-exclusive inclusion, such that apparatus, device or method that comprises a list of components or steps does not include only of those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

Reference will now be made to the apparatus for mixing multiphase flowing particles, and is explained with the help of figures. The figures are for the purpose of illustration only and should not be construed as limitations on the arrangement. Wherever possible, referral numerals will be used to refer to the same or like parts.

FIG. 1 is an exemplary embodiment of the present disclosure which illustrates a perspective view of an apparatus (100) for mixing multiphase flowing particles. The apparatus (100) comprises of a conduit (100a) for conveying/transporting multiphase flowing particles from one place to another place. The conduit (100a) comprises of an inlet side (103) through which the multiphase flow is admitted, and an outlet side (104) for discharging out the multiphase flowing particles. The conduit (100a) has a predetermined cross-sectional area and length. In an embodiment of the present disclosure, the cross-section of the conduit (100a) is uniform, including but not limiting to rectangular, square, triangular, U-shaped, circular or any other cross-section which serves the purpose. In another embodiment of the present disclosure, the cross-sectional area of the conduit (100a) is variable across the length of the conduit (100a).

The variable cross section of the conduit (100a) includes but not limiting to tapered rectangular, square, circular and the like. Generally, the length of the conduit (100a) is relatively higher as compared to cross-sectional dimensions i.e. the width and the height. In an embodiment of the present disclosure, the conduit (100a) for conveying the multiphase flowing particles includes but not limiting to a channel and a pipe. In an embodiment of the present disclosure, the conduit (100a) for conveying the multiphase flowing particles is constructed using materials such as but not limiting to concrete, composite material, high density polymer material and metals.

The multiphase particles that are admitted from the inlet side (103) of the conduit (100a) flow with a definite velocity along the longitudinal axis A-A towards the outlet side (104) of the conduit (100a). During the flow of multiphase flowing particles, the secondary phase settles in relatively lower portion of the conduit (100a), while primary phase flows over the secondary phase. To avoid such settling, the mixing apparatus (100) is provided with at least one flow diverter (101) and the at least one flow element (102).

The flow diverter (101) (best shown in FIG. 3) is configured to divert the multiphase flowing particles into a plurality of flow streams. The flow diverter (101) is generally placed along the longitudinal axis A-A proximal to inlet side (103) of the conduit (100a) and is positioned on the bottom surface of the conduit (100a). Once the multiphase flowing particles contacts the diverter (101), it separates or diverts the multiphase flowing particles into a plurality of flow streams.

Further, the mixing apparatus (100) is provided with at least one flow element (102) disposed on at least one side of the conduit (100a). In an exemplary embodiment of the present disclosure, a plurality of flow elements (102) is disposed on either side of the conduit (100a). Generally, the plurality of flow elements (102) is disposed at an angle to the flow direction of plurality of flow streams. The plurality of flow streams which are diverted by the diverter flow towards the plurality of flow elements (102), and each of the plurality of flow element (102) is configured to inject fluid onto the multiphase flowing particles at a velocity greater than that of multiphase flowing particles. This high velocity injected fluid creates a turbulent zone by generating a swirling flow, which results in mixing of secondary phase with the primary phase. A detailed explanation on mixing of multiphase particles will be reflected in subsequent paragraphs of the detailed description.

Figure 2:
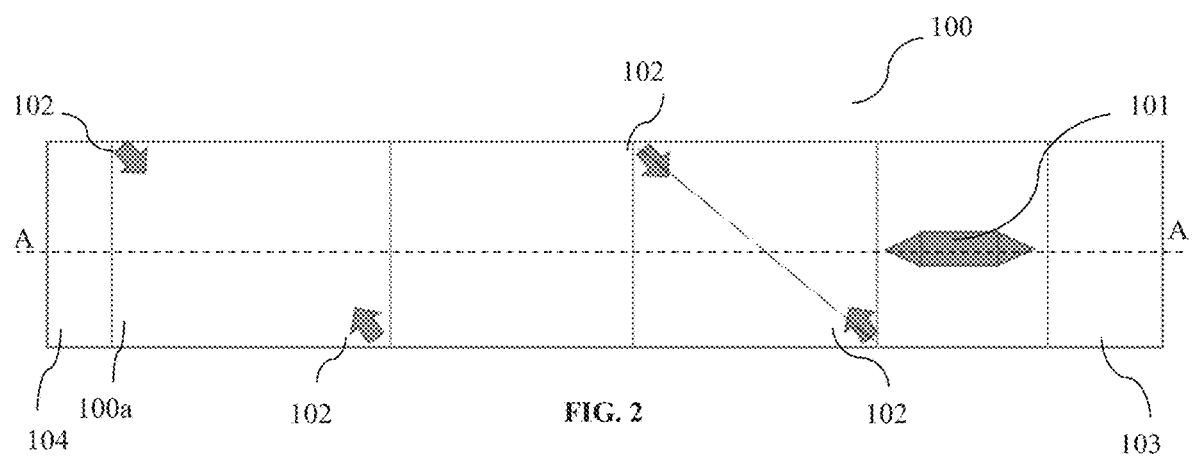
FIG. 2 illustrates schematic top view of the mixing apparatus of the present disclosure according to some embodiment of the present disclosure.

FIG. 2 is an exemplary embodiment of the present disclosure which illustrates top view of the mixing apparatus (100) for mixing multiphase flowing particles. As shown in FIG. 2, the conduit (100a) is provided with a plurality of flow elements (102) on either sides of the conduit (100a) and a diverter (101) positioned proximal to inlet side (103). The multiphase flowing particles are discharged from the inlet side (103) of the conduit (100a) so that the flow takes place along the length of the conduit (100a) towards outlet side (104). The flow diverter (101) is configured to separate the flow into a plurality of flow streams. The shape of the flow diverter (101) is such that when a flowing fluid strikes one of its edges in vertical plane, the flow gets separated, without significant change in the velocity of the multiphase flow. In other words, a flow diverter (101) is an obstructing member placed in the flow path of multiphase flowing fluid which is configured to separate the flow without affecting the flow velocity of primary phase. In an embodiment of the present disclosure, the shape of the flow diverter (101) includes but not limiting to triangle, rhombic and hexagonal. Further, the flow diverter (101) is positioned along the axis A-A of the conduit (100a) in such a way that two vertical faces diverge in the direction of flow, with one of the intersection corners transverse to longitudinal axis of the conduit in a vertical plane. When the multiphase flowing particles strike this intersection corner, flow separation takes place with two or more flow streams moving along two diverging vertical faces of the flow diverter (101). The plurality of flow streams after separation is directed towards the plurality of flow elements (102) located on either sides of the conduit. Furthermore, in one embodiment, the flow elements (102) are provisioned at bottom sides of the conduit (100a).

Further, as shown in FIG. 2, a plurality of flow elements (102) are provisioned on either side of the conduit (100a). In an exemplary embodiment of the present disclosure, the plurality of flow elements (102) is disposed at an angle to the direction of flowing stream and outlet of each of the plurality of flow elements (102) are oriented to be diagonally opposite to each other, at predetermined distances along the length of the conduit (100a). Each of the plurality of flow elements (102) is configured to inject fluid onto the multiphase flowing particles with a velocity greater than the flow velocity of multiphase flow such that, the fluid injected through the diagonally opposite oriented outlets of respective plurality of flow elements (102) have a diagonally intersecting fluid stream. In an embodiment of the present disclosure, the flow element (102) includes but not limiting to nozzles, orifices and jet impingers. In an embodiment of the disclosure, the fluid supplied though the flow elements (102) is a part of bulk flow. A fraction of fluid containing secondary phase particles from the main bulk flow is drawn, using pumps, at a required fluid pressure. This fraction of fluid is injected back into bulk flow (i.e. into the multiphase flow), and is directed on to the plurality of flow stream by the flow elements (102) at a velocity higher than that of the bulk flow. In alternative embodiment of the disclosure, the fluid injected by the flow elements (102) on to the plurality of flow streams is separately taken form a fluid source. The high velocity fluid injected by each of the plurality of flow elements (102) induces a swirling flow in the multiphase flow, resulting in the formation of a highly turbulent zone. This causes agitation of secondary phase in vertical plane causing the movement of secondary phase from top to bottom and vice versa. This is because, secondary phase being high density particles experience larger centrifugal force during swirling motion as compared to primary phase which is relatively less dense. This causes the orientation of secondary phase along the longitudinal axis A-A of the conduit (100a), and prevents settling or accumulation of secondary phase at the bottom of the conduit (100a). As clearly shown in FIG. 2, the plurality of flow elements (102) are positioned on the conduit (100a), such that the plurality of flow elements (102) on one of the side of the conduit (100a) are positioned diagonally opposite to the plurality of flow elements (102) located on the opposite side. By this configuration of mixing apparatus (100), maximum mixing ratios can be achieved. Further, each of the flow element (102) is fluidly connected to a secondary fluid source (not shown), to receive the fluid at a velocity greater than the velocity of flow of multiphase flowing particles. In an embodiment of the present disclosure, the secondary fluid source includes but not limiting to accumulator, pump, and motor.

Figure 3:
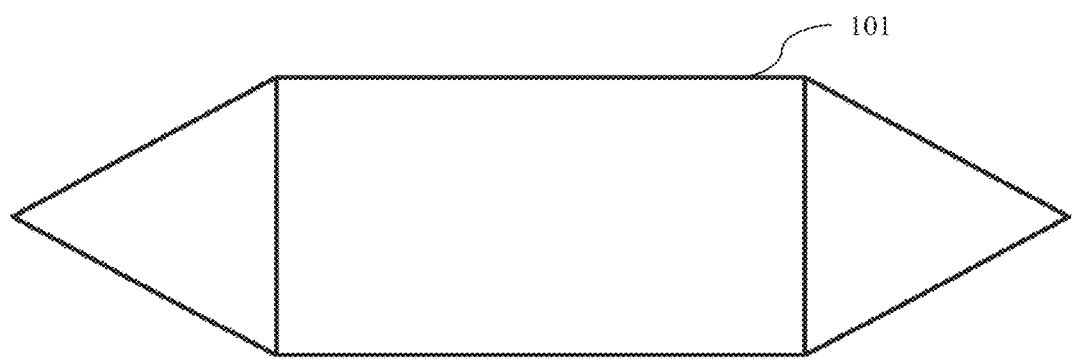
FIG. 3 illustrates schematic top view of a flow diverter according to some embodiment of the present disclosure.

FIG. 3 is an exemplary embodiment of the present disclosure showing schematic top view of a flow diverter (101) used to diver the flow of multiphase flow particles within the conduit (100a). The shape and cross section of the flow diverter (101) is configured to divert flow of the multiphase flowing particles. In one embodiment, the diverter (101) diverts the multiphase flowing particles towards the plurality of flow elements (102) which helps in generating swirling motion in the flow channel (100). In an exemplary embodiment of the present disclosure, the shape of the at least one flow diverter (101) is hexagonal shape. However, it is well understood that a person skilled in the art can employ different shapes of the diverter. Various shapes and forms of diverters which provide the result of diverting flow of the multiphase flowing particles is still considered to be falling within the scope of this disclosure. The at least one flow diverter (101) comprises of an intersecting edge at right angle to the axis A-A of the conduit (100a) in vertical plane. When the multiphase flowing particles strike this intersecting edge of the diverter (101), the multiphase flow separates or diverts into two or more flow streams. Each of the plurality of flowing stream is then directed towards the plurality of flow elements (102), where it is subjected to swirling effect by the fluid injected by the plurality of flow elements (102). The flow diverter (101) comprises of two vertical faces inclined at predefined angles to the axis A-A of the conduit (100a), to direct the plurality of flow streams towards the plurality of flow elements (102).

Figure 4:
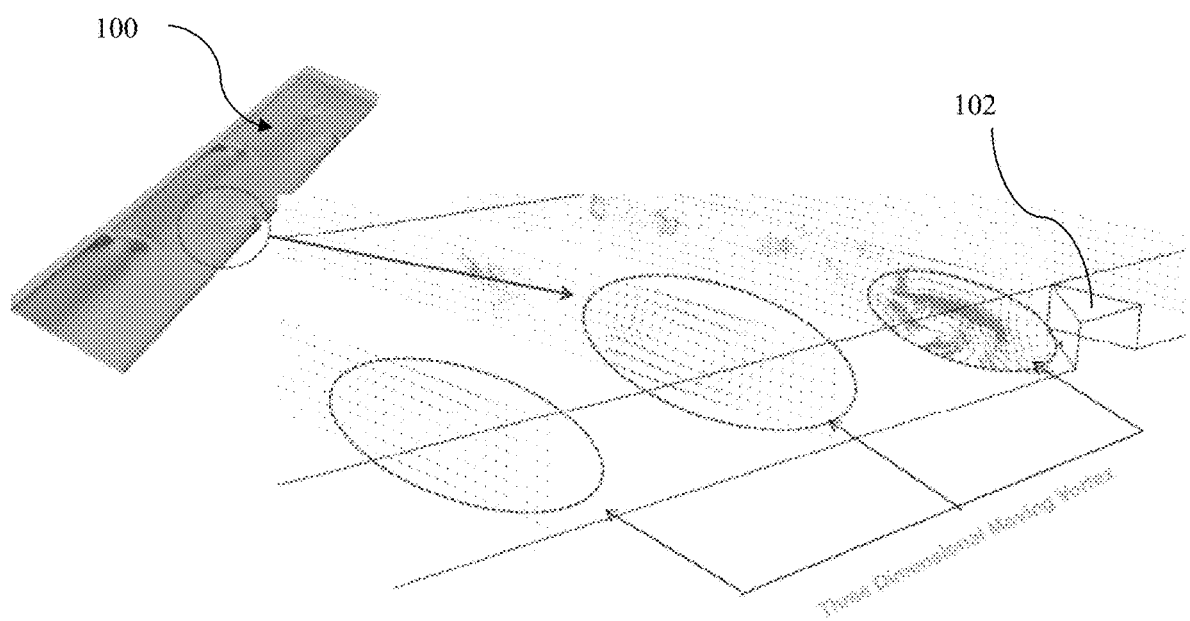
FIG. 4 illustrates Computational Fluid Dynamics (CFD) vector plot of induced three dimensional mixing in the conduit of mixing apparatus of FIG. 1.

FIG. 4 is exemplary embodiment of the present disclosure which illustrates Computational Fluid Dynamics (CFD) results of vector plot portraying generation of swirling flow or vortex formation near the flow elements (102) and it is seen being carried forward. As shown in the FIG. 4, the plurality of flow elements (102) for injecting fluid onto the multiphase flowing particles, are positioned diagonally opposite to each other on the bottom surface of conduit (100a) in the downstream after the flow diverter (101). The multiphase flowing particles are channelized towards the flow elements (102) by the flow diverter (101). The injected fluid with a relative high velocity impinges on the diverted flow, resulting in local vortex zone with high swirling eddies ensuring mixing of primary and secondary phases in the conduit (100a). The secondary phase is carried from bottom to top and vice versa in the conduit (100a), helping to achieve better reaction to mixing scale ratios and mass transfer. The swirling flow/vortex is in the direction of flow and hence any local recirculation zones or stagnation is also avoided ensuring in efficient transfer of flow particles.

Figure 5:
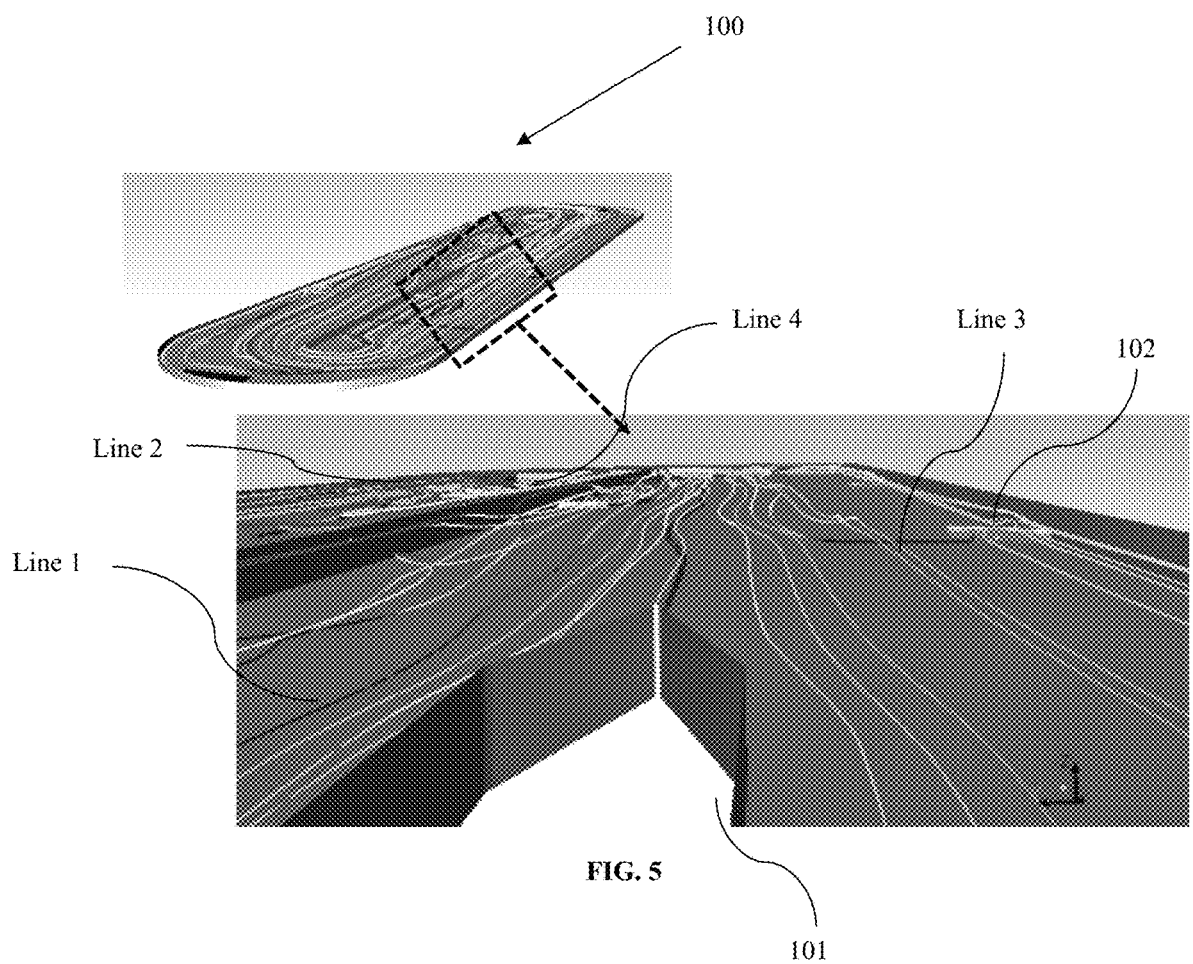
FIG. 5 illustrates Computational Fluid Dynamics (CFD) results of particle movement as a function of height due to induced three dimensional mixing in the conduit of mixing apparatus.

FIG. 5 is an exemplary embodiment of the present disclosure which illustrates Computational Fluid Dynamics (CFD) results of particle movement as a function of height due to induced swirling flow resulting in mixing of multiphase flowing particles. As shown in the FIG. 5, the multiphase flowing particles enter the conduit (100a) from the inlet (103). The denser particles (secondary phase) in the flow will generally be at the bottom side of the conduit (100a). Once the flow reaches the flow diverter (101) area, and hits the flow diverter (101), it will be diverted into two or more flow streams along the flow axis A-A, and move towards the one or more flow elements (102) provided in the conduit (100a). The distribution of secondary phase throughout the conduit (100a) along its entire depth is evident from the flow lines shown in FIG. 5. The lines 2 indicate the presence of secondary phase at the top surface of the conduit (100a); the lines 3 indicate the presence of secondary phase at the middle, while lines 1 indicate the distribution of secondary phase at the bottom surface of the conduit (100a).

In one exemplary embodiment of the present disclosure, the conduit (100a) of the present disclosure can be used in biological continuous flow cultivation systems (600) such as but not limiting to raceway ponds. The raceway ponds are used for culturing/cultivation of organisms, and more specifically, for culturing photosynthetic organisms such as algae. In these raceway ponds, vertical mixing is important for better nutrient homogenization and mass transfer. Photosynthetic organisms need to be exposed to light at regular intervals to meet their metabolic needs, which improves biomass production. Hence, in these raceway ponds, algae and nutrients need to be continuously mixed in the flow so as to maintain solid particles in suspended state, which results in better exposure of these photosynthetic organisms (i.e. algae and nutrients) to light.

Figure 6:
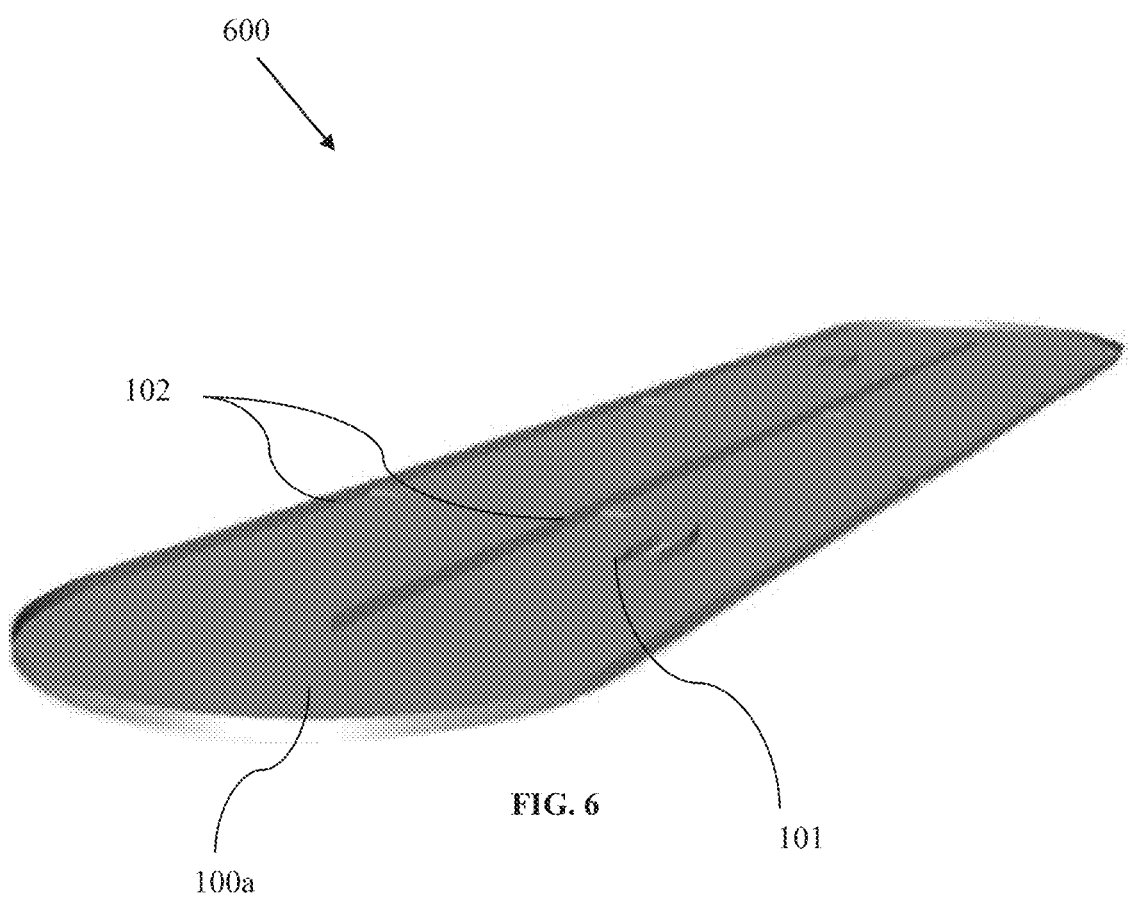
FIG. 6 illustrates perspective view of the apparatus for culturing photosynthetic organisms employed with the mixing device, according to some embodiment of the present disclosure.

The conduit (100a) can be configured as raceway ponds for cultivation of biological organisms (best shown in FIG. 6). In raceway ponds, water along with ingredients required for cultivation of photosynthetic organisms are made to flow continuously. In such biological cultivation systems, it is required that the solid particle in the flow mixture should be kept in suspended state for purposes such as but not limiting to exposure of biological material to light, including but not limiting to sun light. The solid particles should be agitated to cause uniform distribution of the biological organisms in the primary phase, in order to achieve uniform mixing of the biological organisms. In order to achieve the same, the components including but not limiting to solid mass such as photosynthetic organisms and other ingredients such as water and nutrients are made to flow continuously through a conduit (100a) of the present disclosure as multiphase flow. When flow is directed towards the flow diverter (101), it gets separated or diverted into two or more flow streams and move towards the flow elements (102) provided in the conduit (100a). This is followed by injecting a fluid by one or more flow elements on the plurality of flow streams, which results in mixing of the solid particles with the water, and thereby maintaining solid particles in suspended state. In an embodiment of the disclosure, the fluid supplied though the flow elements is a part of continuous flow (i.e. multiphase flow). A fraction of fluid containing secondary phase particles is sucked from the continuous flow, using pumps, at a required fluid pressure. This fraction of fluid is injected back into continuous flow (i.e. into the multiphase flow), and is directed on to the plurality of flow streams by the flow elements (102) at a velocity higher than that of the continuous flow. In alternative embodiment of the disclosure, the fluid injected by the flow elements is a fluid taken from a separate fluid source. This injected fluid containing secondary phase particles flows in loops inside the continuous flow, resulting in local vortex zone which creates high swirling flow. This swirling flow results in movement of secondary phase particles from top to bottom and vice versa, inside the raceway pond. This in turn results in mixing of the flow particles such as water and the solid particles (i.e. algae and nutrients) in the multiphase flow conduit (100a), thereby resulting in exposure of biological material to light and better mass transfer. This improves process efficiency of the biological cultivation system, and the process is economical with very less energy consumption.

In the above paragraph of present disclosure, the mixing arrangement is explained with the help of cultivation of photosynthetic organism (one of the field of applications of the mechanical mixers) as an example. However, such example should not be construed as only application. Thus, person skilled in the art can envisage various other applications where need exists.

INDUSTRIAL APPLICABILITY

The apparatus for mixing multiphase flowing particles as disclosed in the present disclosure finds extensive applications in fields such as but not limiting to biological cultivation systems, mineral ore industry, de-settling of sludge in oil and gas refineries, sewage and waste water treating plants.

ADVANTAGES

The present disclosure provides a multiphase mixing apparatus which facilitates effective mixing of dispersed phase, thereby eliminating the need for auxiliary or additional devices such as mechanical mixers. This results in substantial energy savings as compared to other mixing apparatuses utilizing mechanical mixers and other such devices.

The present disclosure provides an apparatus for mixing multiphase flowing particles which includes the use of a plurality of flow elements such as but not limiting to nozzles, orifices and jet impingers which inject fluids at a high velocity and low pressure. This injection of fluid with high velocity will not have any effect on pressure of multiphase flow and hence will not result in loss of pressure and kinetic head of the multiphase flow, unlike their mechanical mixer counterparts.

The present disclosure provides an apparatus for mixing multiphase flowing particles which involves injection of high velocity fluid which creates swirling flow that is spread over a significant distance along the length of the conduit. This facilitates the installation of flow devices only at few positions along the length of conduit, which makes the overall system compact, requiring less attention for maintenance. This also results in subsequent savings in energy required for operation.

EXEMPLARY EXPERIMENTAL DATA

A comparative study has been conducted between conventional mixing devices such as paddle wheels, and a mixing device of the present disclosure. For comparative study, cultivation of photosynthetic organism such as algae is considered.

The extent and efficiency of mixing of multiphase flowing particles for photosynthetic cultivation of algae is demonstrated using 3D Computational Fluid Dynamics (CFD) in the conduit of a raceway pond. In the exemplary embodiment, the conduit has an operating depth of 0.3 m, a width of 10 m and a length of 50 m. The inlet side of the conduit is admitted with primary phase i.e. water, with a velocity range of 0.2-0.4 m/sec. In the first case, a paddle wheel mixer is provided in the conduit and is allowed to run at an angular velocity of 18 rpm. The secondary phase particles i.e. algae along with nutrients are then discharged into the primary phase (water) at the bottom of conduit and then at the top of the conduit.

After the simulation is completed, path lines (coloured lines) were used to depict the actual path of secondary phase i.e. algae and nutrients in this case, which in turn is used to explain the flow behavior.

Figures 7A, 7B:
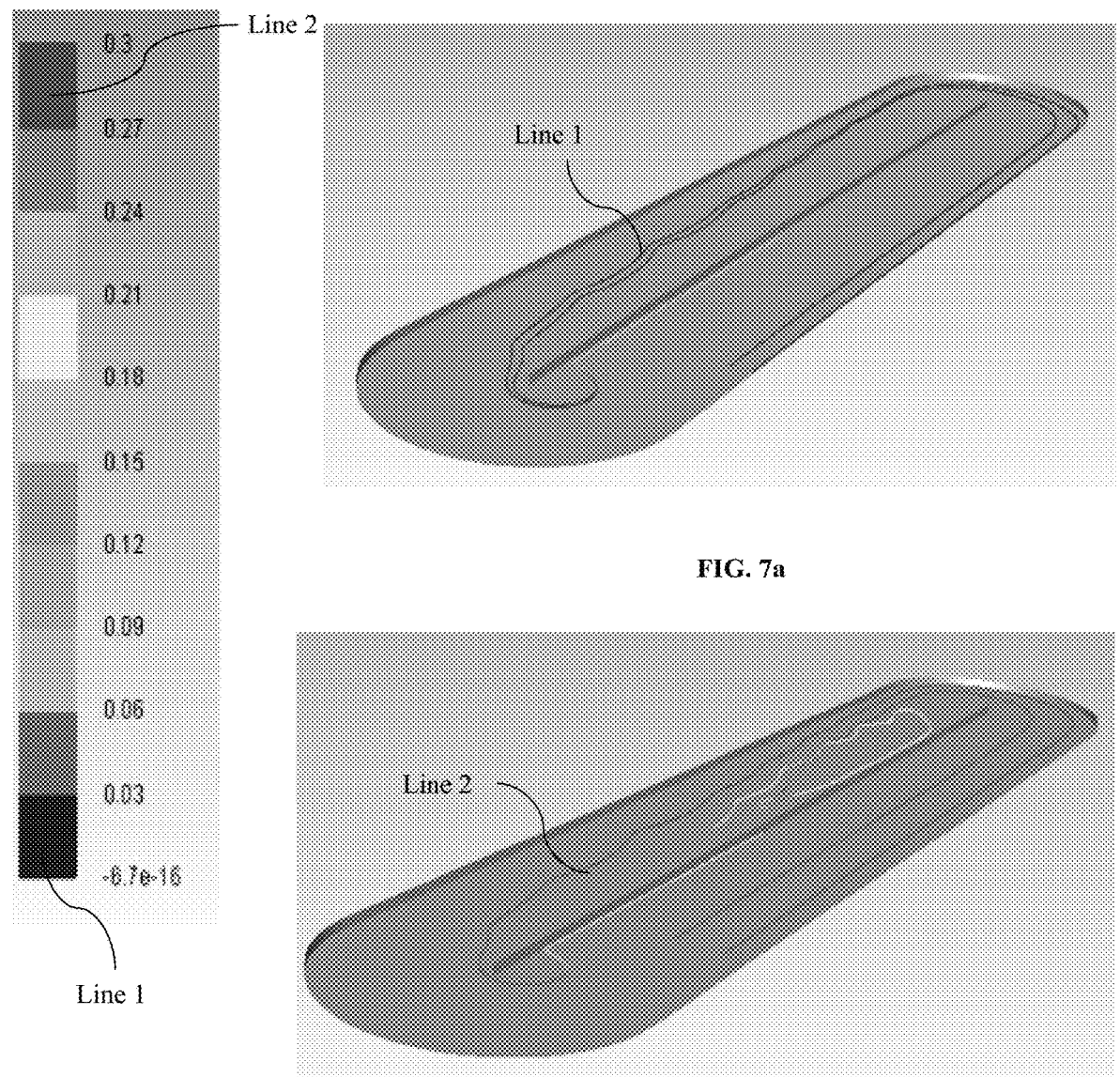
FIGS. 7a and 7b illustrate Computational Fluid Dynamics (CFD) results of particle movement as a function of height due to induced three dimensional mixing in the apparatus for culturing photosynthetic organisms operated by paddle wheel mixers.

Referring now to FIG. 7a, which shows a raceway pond with secondary phase particles (algae) discharged at the bottom of conduit, by sucking a fraction of fluid from the multiphase flow and injecting back into it by flow elements. From FIG. 7a, it is evident that the secondary phase particles move only at the bottom of the raceway pond as clearly shown by line 1. The line 1 depicts the flow path of secondary phase particles (algae and nutrients) as a function of height of the conduit. This is because of lack of vertical mixing of the secondary phase in multiphase flow, which causes the flow to become stratified. In other words, mixing is dominant in horizontal plane than in vertical plane inside the raceway pond. Similarly, referring to FIG. 7b, it is evident that when the secondary phase particles are discharged at the top of the conduit, by sucking a fraction of fluid from multiphase flow and injecting back into it by flow elements, the secondary phase particles move only along the top of the conduit as clearly shown by line 2. Hence, it is evident from FIGS. 7a and 7b that the secondary phase particles move only at the bottom and top of the conduit, when discharged from bottom and top of the conduit respectively, resulting in improper mixing.

Figure 8:
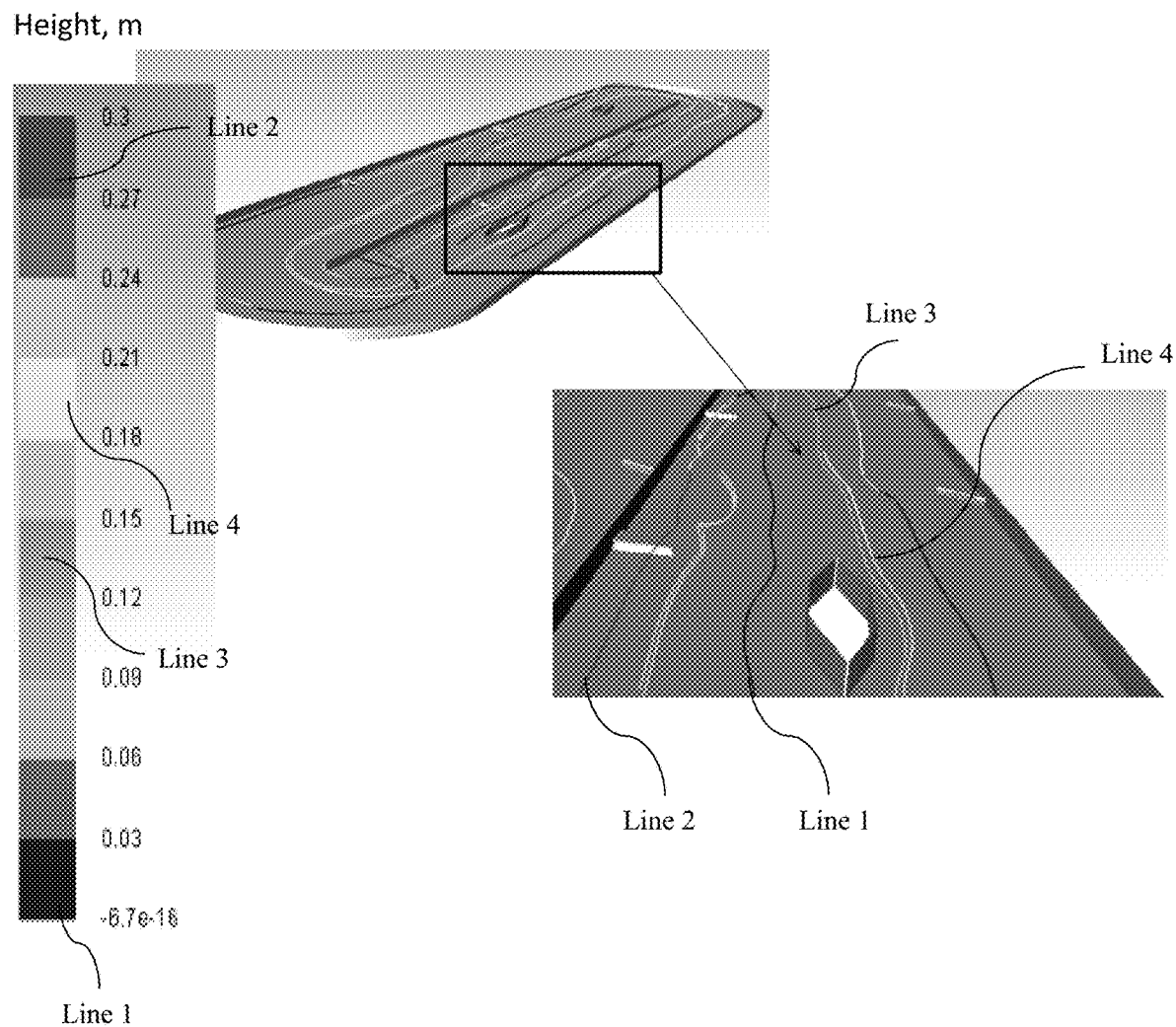
FIG. 8 illustrates Computational Fluid Dynamics (CFD) results of particle movement as a function of height due to induced three dimensional mixing in the apparatus for culturing photosynthetic organisms mixing apparatus, according to one exemplary embodiment of the present disclosure.
Figure 9:
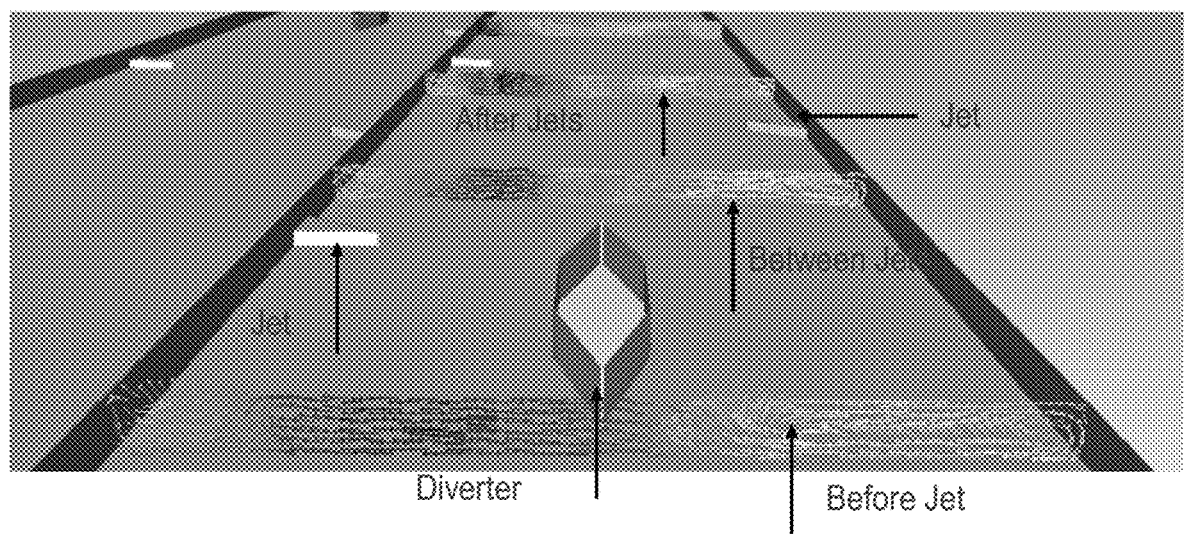
FIG. 9 illustrates vector plot showing swirl flow across entire length of the conduit through which multiphase flowing particles are discharged, according to one exemplary embodiment of the present disclosure.

In the second case, as depicted in FIG. 8, the simulation is carried out in the same raceway pond, by incorporating mixing apparatus of the present disclosure. In this case, the primary phase (water) flows continuously through the raceway pond at a velocity of 5 cm/sec (0.05 m/sec). A fraction of multiphase flow containing secondary phase particles (algae and nutrients) is sucked from the bulk flow and is admitted (pumped) from the bottom of the conduit by the flow elements, at a velocity greater than the velocity of the flow of the main flow. Thus, a swirling motion of flow is created in the conduit after the jet (clearly shown in FIG. 9). This swirling flow depends on the positioning of the flow elements. In this case, the flow elements are placed at the bottom of the conduit, where flow elements on one of the sides of conduit are diagonally opposite to the flow elements on the other side of the conduit. Due to creation of vortex swirling motion in the conduit, the secondary phase particles (algae and nutrients) traverse across the pond depth (from bottom to top and vice versa) as it moves along the length of the conduit. This is clearly depicted by path lines 1, 2, 3 and 4, as a function of height of the conduit, in FIG. 8. Hence it is evident that efficient mixing takes place in the mixing apparatus disclosed in the instant invention compared to paddle wheel mixers (mechanical mixers).

Figure 10:
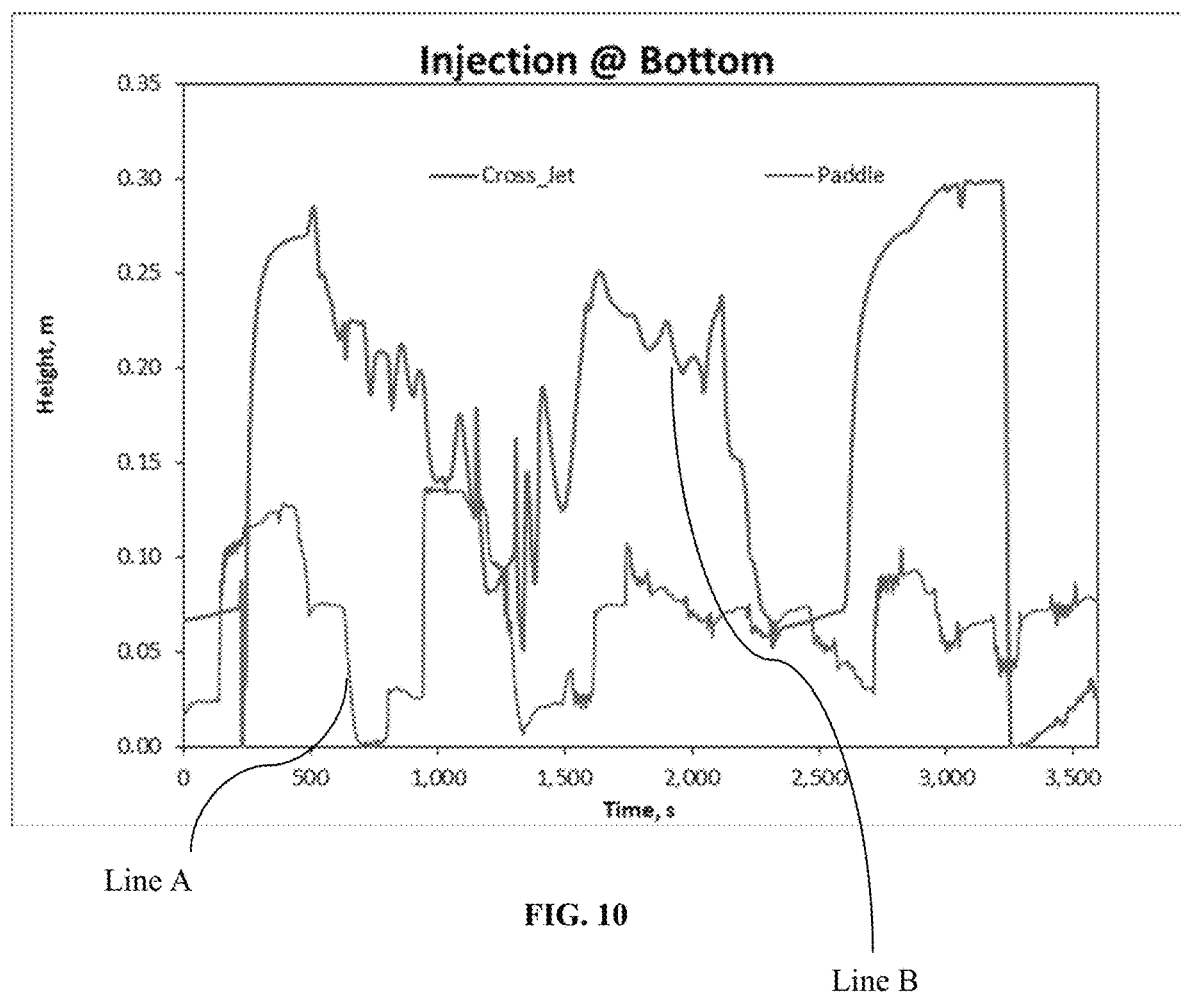
FIG. 10 illustrates the comparison between results of particle movement as a function of height operated by arrangements shown in FIGS. 7a-7b and 8.

Further, FIG. 10 illustrates the comparison graph between raceway pond operated with paddle wheels, and raceway pond provided with flow diverter and flow elements. The movement of secondary phase particles (algae) as a function of height in the conduit operated by paddle wheel mixer is shown by the line A. On the other hand, the movement of secondary phase particles (algae and nutrients) as a function of height in the mixing apparatus of instant invention is shown by the line B. This shows that better mixing ratios can be achieved with the mixing apparatus of the present disclosure (with flow diverter and flow elements) in comparison with mechanical mixer counterparts.

Further, the Table 1 shown below provides a comparison on energy consumption for raceway ponds operated with paddle wheel mixers and raceway ponds operated with diverter and flow elements (with 8 number of diagonally positioned jets). As is evident from the table, energy consumed by the diverter-flow element operated mixing apparatus is considerably less compared to paddle wheel operated mixing apparatus. A better mixing ratio is achieved in addition to lesser energy consumption in mixing apparatus operated by diverter and flow elements.

TABLE 1

| Design 500 SQM | Operating Velocity m/s | Operating Depth m | Power Consumption Kw |
|---|---|---|---|
| Paddle | 0.3 | 0.3 | 1.25 |
| Cross Jet | 0.05 | 0.3 | 1.2 |

EQUIVALENTS

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

TABLE OF REFERRAL NUMERALS

| Reference Number | Description |
| --- | --- |
| 100 | Mixing apparatus |
| 100a | Conduit |
| 101 | Flow diverter |
| 102 | Flow elements |
| 103 | Inlet side of conduit |
| 104 | Outlet side of the conduit |
| A-A | Multiphase flow axis |
| Lines 1-4 | Flow path lines which indicate secondary phase flow as a function of conduit height |
| Line A | Flow path line which indicates secondary phase flow in conduit fitted with paddle wheel |
| Line B | Flow path line which indicates secondary phase flow in conduit of present disclosure |

We claim:

1. An apparatus for mixing multiphase flowing particles, the apparatus comprising:
   a conduit adapted to channelize the multiphase flowing particles;
   at least one flow diverter positioned in the conduit, wherein the at least one flow diverter is adapted to divert flow of the multiphase flowing particles into a plurality of flow streams; and
   a plurality of flow elements disposed on either sides of the conduit along at least one of the plurality of flow streams, an outlet of each of the plurality of flow elements provisioned on one of the sides of the conduit is oriented diagonally opposite to the outlet of corresponding at least one of the plurality of the flow elements provisioned on other side of the conduit, wherein the plurality of flow elements are configured to inject fluid onto the plurality of flow streams at a velocity greater than the velocity of the plurality of flow streams, such that, the fluid injected, through the diagonally opposite oriented outlets of the respective plurality of flow elements to have a diagonally intersecting fluid stream, to induce a swirling flow of at least one of the plurality of flow streams, thereby facilitating mixing of the multiphase flowing particles in the conduit.

2. The apparatus as claimed in claim 1, wherein the at least one flow diverter is positioned at the bottom of the conduit.

3. The apparatus as claimed in claim 2, wherein the shape of the at least one flow diverter is at least one of triangular, rhombic and hexagonal.

4. The method as claimed in claim 3, wherein the swirling flow of at least one of the plurality of flow streams is induced along the length of the conduit.

5. The apparatus as claimed in claim 1, wherein the conduit comprises an inlet side and an outlet side.

6. The apparatus as claimed in claim 1, wherein the at least one flow diverter is positioned proximal to inlet side of the conduit.

7. The apparatus as claimed in claim 6, wherein the plurality of flow elements are at least one of nozzles, orifices and jet impingers.

8. The apparatus as claimed in claim 6, wherein the plurality of flow elements are positioned at a predetermined angle to the longitudinal axis of the conduit, to induce the swirling flow of at least one of the plurality of flow streams.

9. An apparatus for culturing photosynthetic organisms comprising an apparatus for mixing multiphase flowing particles as claimed in claim 1.

10. A method for mixing multiphase flowing particles, the method comprising:
- channelizing the multiphase flowing particles through a conduit;
- diverting flow of the multiphase flowing particles into a plurality of flow streams by at least one flow diverter positioned in the conduit; and
- injecting fluid onto the plurality of flow streams at a velocity greater than the velocity of the plurality of flow streams, wherein an outlet of each of a plurality of flow elements provisioned on one of the sides of the conduit is oriented diagonally opposite to the outlet of corresponding at least one of the plurality of the flow elements provisioned on other side of the conduit such that, the fluid injected, through diagonally opposite oriented outlets of the respective plurality of flow elements have a diagonally intersecting fluid stream, to induce a swirling flow of at least one of the plurality of flow streams, thereby facilitating mixing of the multiphase flowing particles in the conduit.

\* \* \* \* \*